United States Patent [19]

Grayston et al.

[11] Patent Number: 5,008,186

[45] Date of Patent: Apr. 16, 1991

[54] DETECTION OF UNIQUE CHLAMYDIA STRAIN ASSOCIATED WITH ACUTE RESPIRATORY DISEASE

[75] Inventors: J. Thomas Grayston; Cho-chou Kuo, both of Seattle; San-pin Wang, Redmond, all of Wash.

[73] Assignee: The Board of Regents of the University of Washington, Seattle, Wash.

[21] Appl. No.: 517,390

[22] Filed: Apr. 30, 1990

Related U.S. Application Data

[63] Continuation of Ser. No. 281,913, Dec. 7, 1988, abandoned, which is a continuation of Ser. No. 858,380, May 1, 1986, abandoned.

[51] Int. Cl.$^5$ ............... G01N 33/53; G01N 33/566; C12N 15/08; C07K 15/28
[52] U.S. Cl. ............................. 435/7.36; 435/172.2; 435/177; 435/240.2; 435/240.26; 435/240.27; 435/804; 436/501; 436/536; 436/540; 436/542; 436/548; 530/387
[58] Field of Search ............... 435/7, 177, 804, 172.2, 435/240.2, 240.26, 240.27; 436/501, 528, 530, 540, 542, 548, 824, 536; 530/387, 389

[56] References Cited

U.S. PATENT DOCUMENTS

| | | | |
|---|---|---|---|
| 4,407,943 | 10/1983 | Cole et al. | 436/528 X |
| 4,497,899 | 2/1985 | Armstrong et al. | 436/534 X |
| 4,582,791 | 4/1986 | Khanna et al. | 436/548 X |

OTHER PUBLICATIONS

Kuo, C-c et al., "Primary Isolation . . . in HeLa 229 Cells Treated with DEAE-Dextran", J. Inf. Diseases 125(6), 665-8 (Jun. 1972).

Stephens, R.S., et al., "Monoclonal Antibodies to *Chlamydia trachomatis* . . . ", J. Immunology 128(3), 1083-1089 (1982).

Wang, S-p, et al., "Immunotyping of *Chlamydia Trachomatis* with Monoclonal Antibodies", J. Inf. Des 152(4) 791-800 (1985).

*Primary Examiner*—Esther L. Kepplinger
*Assistant Examiner*—Janelle Graeter
*Attorney, Agent, or Firm*—Seed and Berry

[57] ABSTRACT

Methods for detecting a unique strain of chlamydia associated with acute respiratory disease are disclosed. These methods utilize monoclonal antibody directed against an antigenic determinant of the TWAR strain of chlamydia. Also disclosed is a method for determining the presence of antibodies to the TWAR strain, utilizing elementary bodies of the TWAR strain as antigen.

29 Claims, 1 Drawing Sheet

DETECTION OF UNIQUE CHLAMYDIA STRAIN ASSOCIATED WITH ACUTE RESPIRATORY DISEASE

CROSS-REFERENCE TO RELATED APPLICATION

This application is a continuation of U.S. application Ser. No. 07/281,913 filed Dec. 7, 1988, now abandoned, which is a continuation of U.S. patent application Ser. No. 858,380, filed May 1, 1986, now abandoned under C.F.R. Section 1.62.

DESCRIPTION

1. Technical Field

The present invention relates to the production of monoclonal antibodies in general, and more specifically, to monoclonal antibodies that bind to a newly discovered Chlamydia strain associated with respiratory infection, and to methods for detecting this new Chlamydia strain in biological samples.

2. Background Art

Chlamydia are obligate intracellular parasites that are ubiquitous throughout the animal kingdom and are known to cause a variety of diseases. The chlamydia genus has two recognized species, *C. trachomatis* and *C. psittaci. C. trachomatis*, the species that is a primary human pathogen, causes ocular, respiratory, and urogenital infections. *C. trachomatis* can initially colonize the mucous membranes, including the conjunctiva, nasopharynx, rectum, urethra, and cervix, after which the infection may spread to affect the deeper organ systems.

The other species of chlamydia, *C. psittaci*, is responsible for the human respiratory disease, psittacosis. Psittacosis is usually contracted by exposure to infected birds, outbreaks of psittacosis having occurred in association with turkey and duck processing plants and among pet shop clientele. The disease often resembles atypical pneumonia and may range in severity from mild to fatal. Although epidemics of such pneumonia have usually been traced to infected birds, an avian vector is not always found. For instance, during a radiographic survey in northern Finland in 1978, an epidemic of mild pneumonia was found in two communities; however, avian transmission was not detected.

Seroepidemiological studies have implicated an unusual strain of chlamydia in this and several other pneumonia epidemics in northern Europe. This new strain of chlamydia, referred to as "TWAR" (after the first two isolates, TW-183 and AR-39), has more recently been established as an important respiratory pathogen, being responsible for perhaps up to 12% of the atypical pneumonia cases in adult populations studied. However, most TWAR infections have been inadequately treated with antibiotics due to a mistaken belief that the causative agent was *Mycoplasma pneumoniae* or influenza virus A or B. While antibiotic treatment with erythromycin in the low doses used for *M. pneumoniae* is effective against Mycoplasma infection, erythromycin at this dose is not effective against chlamydial infections. Further, TWAR infections are often characterized by a relapsing illness after an apparent resolution of symptoms.

In light of this association between the TWAR strain of chlamydia and acute respiratory disease, it would be highly desirable to provide an accurate and cost-effective method for diagnosing the presence of a TWAR strain, thereby permitting an effective antibiotic treatment of the primary infection. The present invention provides such a method and is further characterized by other related advantages.

DISCLOSURE OF THE INVENTION

Briefly stated, the present invention provides methods for detecting the presence of a TWAR strain of chlamydia in biological samples. These methods utilize a monoclonal antibody directed against an antigenic determinant of the TWAR strain of chlamydia.

In one aspect of the invention, the method comprises the steps of (a) exposing a biological sample suspected of containing the TWAR strain to a labeled monoclonal antibody directed against an antigenic determinant of the TWAR strain; and (b) detecting the presence of immunocomplexes formed between the monoclonal antibody and the TWAR strain.

A related method for detecting the presence of the TWAR strain comprises (a) combining a biological sample suspected of containing the TWAR strain with HeLa cells such that the TWAR strain becomes intracellular; (b) incubating the HeLa cells containing the TWAR strain; (c) exposing the HeLa cells/TWAR strain to a labeled monoclonal antibody directed against an antigenic determinant of the TWAR strain; and (d) detecting the presence of immunocomplexes formed between the TWAR strain and the labeled monoclonal antibody. In a particularly preferred embodiment of the present invention, the step of combining comprises inoculating the HeLa cells with the sample and subsequently centrifuging the inoculated sample onto the HeLa cells. It is also preferable to pretreat the HeLa cells with DEAE-dextran and cyclohexamide.

A third aspect of the present invention discloses a method for determining the presence of antibodies to the TWAR strain of chlamydia in a biological sample. The method generally comprises (a) incubating the biological sample with elementary bodies of the TWAR strain of chlamydia to form a reaction mixture; and (b) analyzing the reaction mixture to determine the presence of antibodies to the TWAR strain. In a preferred embodiment, the step of analyzing comprises contacting the reaction mixture with a labeled specific binding partner for the antibody and detecting the label. In this regard, the specific binding partner may be goat anti-human IgM or goat anti-human IgG.

In all of the methods briefly described above, the monoclonal antibody may be labeled with an enzyme, fluorophore, radioisotope, or luminescer. In this regard, the step of detection would normally be by enzyme reaction, fluorescence, radioactivity, or luminescence emission, respectively.

The methods described above may be applied to a variety of biological samples in order to detect the presence of the TWAR strain of chlamydia or antibodies to the TWAR strain. Bodily secretions, bodily fluids, and tissue specimens are all suitable samples in this regard. Examples of bodily secretions include cervical secretions, trachial-bronchial secretions, and pharyngeal secretions. Suitable bodily fluids include blood, tears, and central nervous system fluid. Examples of tissue specimens include a variety of biopsies, such as a biopsy of lung tissue or fallopian tube tissue. In addition, tissue from substantially all areas may be examined within a postmortem examination, including heart tissue and lung tissue.

In accordance with the present invention, continuous hybrid cell lines are established that produce monoclonal antibodies directed against an antigenic determinant of the TWAR strain of chlamydia for use in the methods described above. In a particularly preferred embodiment, the cell line comprises the hybridoma clone RR 402 or TT 205. Monoclonal antibodies produced by such cell lines are also disclosed.

These and other aspects of the present invention will become evident upon reference to the following detailed description and attached drawing.

BEST MODE FOR CARRYING OUT THE INVENTION

Figures 1A, 1B:
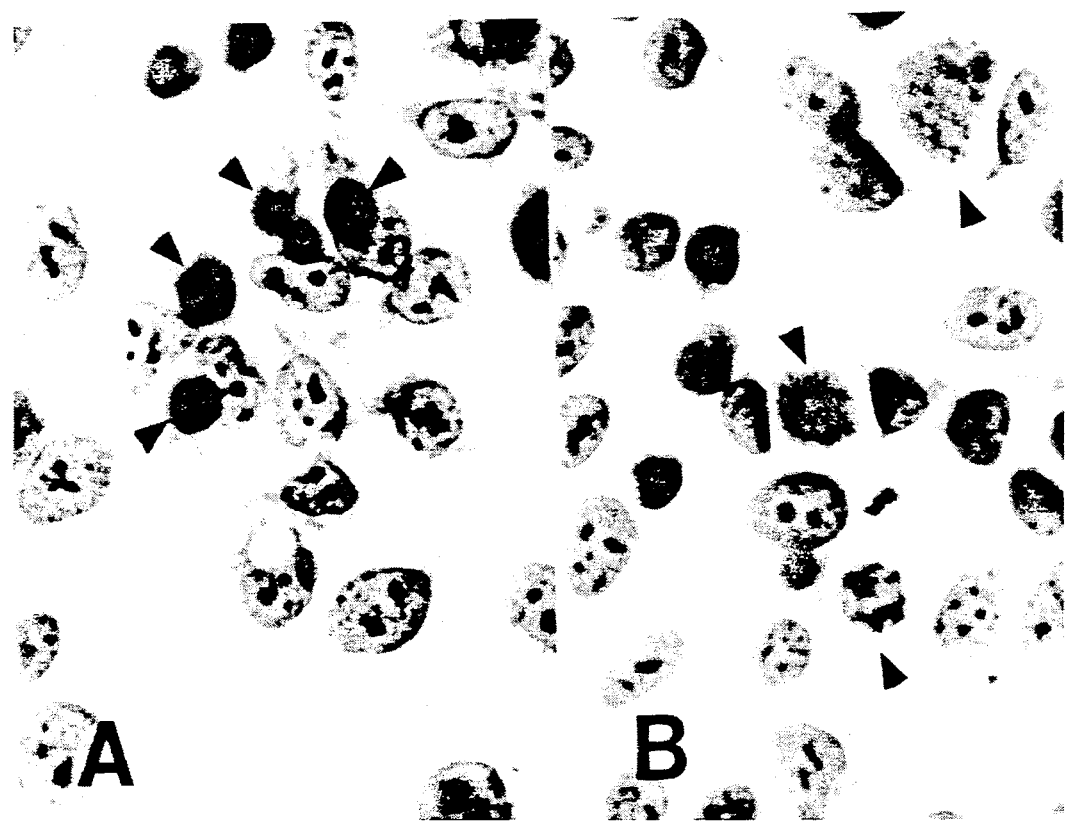
FIG. 1A is a photomicrograph demonstrating TWAR inclusions morphologically typical of *C. psittaci.*
FIG. 1B is a photomicrograph demonstrating the vacuolar structure typical of *C. trachomatis.*

As noted above, seroepidemiological studies have implicated an unusual strain of chlamydia in several pneumonia epidemics in northern Europe and elsewhere. This new strain of chlamydia has been referred to as "TWAR," from the laboratory designations of the first two isolates (TW-183 and AR-39). TWAR has been shown to belong to the genus Chlamydia and has been tentatively classified into one of the two chlamydia species, *Chlamydia psittaci.* This tentative classification is based on the morphology of the inclusions formed by the TWAR organism in cell culture (described in more detail below), the fact that the inclusions are glycogen-negative (while *C. trachomatis* has glycogen-positive inclusions), and the failure of the TWAR strain to react with *C. trachomatis* species-specific monoclonal antibody (R. S. Stephens et al., J. Immunol. 128: 1083, 1982).

While the TWAR strain clearly does not belong to the *C. trachomatis* species, it also exhibits important differences from currently recognized *C. psittaci* strains. TWAR and the other *C. psittaci* strains are immunologically distinct; no cross-reactions with the other *C. psittaci* strains have been found. Further, in the production of monoclonal antibodies against the TWAR strain (more thoroughly described below), no *C. psittaci* species-specific antibodies were detected, only genus- and strain- (TWAR serovar) specific antibodies were found. It is also interesting to note that while a plasmid has been found in all *C. psittaci* and *C. trachomatis* chlamydial strains examined, the TWAR strain has no plasmid. In addition, while all known *C. psittaci* strains have an animal or bird host, no animal or bird host for the TWAR strain has been found. Therefore, it is possible that the TWAR strain will eventually be classified separately from *C. psittaci.* In accordance with the present invention, the TWAR strain is therefore defined to include any chlamydia strain that is morphologically similar to *C. psittaci* and immunologically distinct from currently recognized *C. psittaci* strains.

Hybridoma formation and production of monoclonal antibodies have been shown to be useful in immunodiagnosis of a variety of microbiological diseases. More specifically, monoclonal antibodies allow detection and serological classification of human infections. In addition, these monoclonal antibodies facilitate identification of genus- and species-specific antigens.

As noted above, continuous hybrid cell lines are established which are capable of producing monoclonal antibodies to an antigenic determinant of the TWAR strain of chlamydia. A general protocol for establishing such cell lines includes immunizing an experimental animal, usually a mouse, with an appropriate antigen. Immune spleen cells are then isolated and fused with myeloma or lymphoma cells by exposure to a chemical agent, such as polyethylene glycol. Fused hybrid cells are then incubated in a selective medium, such as HAT medium, that precludes the growth of the malignant cell line. Hybridoma cells are cloned by limiting dilution, and culture supernatants are assayed for secretion of monoclonal antibody having a desired specificity. Large yields of selected monoclonal antibodies may be obtained through ascitic growth of hybridomas in vivo.

In order to obtain monoclonal antibodies that are specific for the TWAR strain of chlamydia, an appropriate TWAR antigen must be prepared. TWAR isolates may be cultured from throat (oropharynx) specimens of patients, either through eukaryotic cell culture or embryonated egg yolk sac culture. Most primary isolates require egg-adaptation of the TWAR strain prior to successful eukaryotic cell culture. In particular, it may be preferable to passage the TWAR isolates once or twice in yolk sac culture and then inoculate them onto cultures of HeLa 229 cells propagated in vials. It is also preferable to pretreat the HeLa cells with DEAE-dextran and cyclohexamide. The TWAR isolates may be adapted to grow in cell culture by repeated culture passages. In particular, approximately 10 or more serial culture passages may be advantageous for adaptation to HeLa cell growth.

Referring now to FIGS. 1A and 1B, photomicrographs are presented showing a HeLa 229 cell monolayer infected with a TWAR strain and a *C. trachomatis,* respectively. FIG. 1A demonstrates TWAR inclusions morphologically typical of *C. psittaci.* The TWAR infection exhibits relatively dense cytoplasmic inclusions that have not indented or displaced the nucleus. In contrast, FIG. 1B demonstrates typical vacuolar inclusions of *C. trachomatis* that indent the nucleus.

The infected cell cultures are normally monitored for TWAR strain infectivity; and when a certain percentage of cells are infected, multiple vial cultures are inoculated in preparation for growth in large culture bottles. In a preferred embodiment, when 50% infectivity is obtained, 20 to 30 vials of HeLa 229 cells may be infected to provide the inoculum for a 32-oz prescription bottle culture. Subsequent serial pasages will increase the number of TWAR strain chlamydia. This adaptation and scale-up will yield a sufficient quantity of TWAR antigen for monoclonal antibody production and screening.

The immunogen for hybridoma production employed within the present invention was purified TWAR antigen. In a preferred embodiment, the antigen is Renografin-purified TWAR elementary bodies (>99% purified). Hybridomas may be prepared by fusion of immune mouse spleen cells with NS-0 myeloma cells, and hybridoma clones secreting antichlamydial antibodies identified. In a preferred embodiment, hybridoma culture supernatants are screened by ELISA. In a particularly preferred embodiment, the ELISA employs peroxidase-conjugated anti-mouse immunoglobulins and a colorimetric detection system. Further testing of monoclonal antibody specificity by a micro-immunofluorescence technique (S. P. Wang and J. T. Grayston, *Amer. J. Ophthal.* 70: 3678, 1970) is also preferred.

TWAR-elicited hybridomas may be intraperitoneally inoculated into syngeneic BALB/c mice. It is preferable to Pristane-prime the mice 2 weeks prior to inoculation. The resultant ascites fluid may be harvested, and monoclonal antibodies purified. In a preferred embodiment, ascitic monoclonal antibodies are affinity purified on a protein-A-sepharose column.

Selected TWAR monoclonal antibodies may be labeled for use within the methods described herein. Preferred labels include enzymes, fluorophores, radioisotopes, and luminescers. These and other labels are well known in the art. A particularly preferred label in this regard is fluorescein. The labeled TWAR monoclonal antibodies may then be examined for genus-, species- and strain-specificity. As shown in Table 1, when employed in a micro-immunofluorescence assay, the TWAR-elicited monoclonal antibodies reacted with TWAR isolates, but not *C. trachomatis* or *C. psittaci*.

TABLE 1

Specificity of TWAR-Elicited Monoclonal Antibodies

| Chlamydial Strains | | Micro-IF Antibody Titer with TWAR-Elicited MAb | ELISA Antibody Titer with Genus-Specific MAb |
|---|---|---|---|
| TWAR - | TW 183 | 6400 | 3200 |
|  | AR 39 | 6400 | 3200 |
|  | AR 277 | 6400 | 3200 |
|  | AR 388 | 6400 | 3200 |
| *C. psittaci* (6 strains) | | 0 | 3200 |
| *C. trachomatis* (15 serovars) | | 0 | 3200 |

Fluoroscein-conjugated TWAR monoclonal antibodies specifically stained TWAR elementary bodies and TWAR inclusion in infected cultured cells, but did not stain other chlamydia. The present invention thus provides a monoclonal antibody that binds to a TWAR-specific antigenic determinant.

Within the present invention, a TWAR-specific monoclonal antibody has been employed in diagnostic assays of biological specimens. In particular, the present invention provides methods for detecting TWAR strains in smears of clinical specimens and in inoculated cell cultures. These methods utilize labeled TWAR-specific monoclonal antibody that binds directly to TWAR-specific antigenic determinants in immobilized specimens. The specimens may be immobilized on a solid support, such as a glass slide, coverslip, or a microtiter well. The specimen or biological sample should also be fixed to the solid support, as by methanol or ethanol fixation. After the sample is fixed or bound to the surface, the sample is exposed to the labeled monoclonal antibody. Alternatively, a labeled second antibody capable of binding to the TWAR-specific monoclonal antibody may be employed. This modification of the method may provide an enhancement in the signal of the label. Identification of TWAR strains in smear specimens by a direct fluorescent antibody technique is rapid, simple, and relatively inexpensive. The smear technique can be used both in clinical settings (early diagnosis, improved opportunity for isolation of the causative organism, follow-up on success of treatment) and in epidemiological settings.

In addition to providing a method for detecting the presence of the TWAR strain, the present invention provides a method for determining the presence of antibodies to the TWAR strain in biological samples. A particularly preferred embodiment for the screening of serum or bodily fluids for TWAR antibodies is the micro-IF assay. Typically, antigen (chlamydia elementary body antigen) is fixed onto a microscopic slide, and the slide incubated with a sample suspected of containing TWAR antibody. A labeled specific binding partner is then added (such as fluorescein-conjugated anti-mouse immunoglobulin) and the reaction observed to determine the presence of antibodies to the TWAR strain.

The following examples are offered by way of illustration and not by way of limitation.

EXAMPLE 1

Growth and Isolation of TWAR Strains

A. Cell Culture Isolation

Specimens of throat (oropharynx) swabs in transport media (sucrose/potassium/glutamate; SPG) from patients with acute respiratory disease were cultured according to a method modified from C. C. Kuo et al. (*J. Infect. Dis.* 125: 665–668, 1972). Each specimen was inoculated onto three vials containing HeLa 229 cell monolayers which had been pretreated with DEAE-dextran (30 ug/ml) and cyclohexamide (0.5–0.8 ug/ml) prior to inoculation. The inoculum was centrifuged onto the cells at 2,200 rpm for 60 minutes at room temperature. The vials were then incubated at 35° C. for 72 hours (passage 1). The monolayer from one of the vials was fixed with methanol and stained with fluorescent antibody to search for inclusions indicative of infection. The other two vials were available to provide inoculum for a second passage.

B. Egg Culture Isolation

Specimens of throat (oropharynx) swabs in SPG transport media from patients with acute respiratory disease were inoculated into the yolk sac of embryonated eggs, 6 to 8 days of age, according to the method of J. T. Grayston et al. (*Proc. Soc. Exp. Biol. Med.* 103: 596, 1960). Streptomycin was added to the specimen until a concentration was reached that gave 10 mg per egg on inoculation. The eggs were incubated at 35° C. and candled daily. Upon death, or survival for 12 to 13 days, yolk sacs were harvested and stained by a modified Macchiavello staining method to look for elementary bodies of chlamydia. When TWAR monoclonal antibody conjugated to fluorescein became available for staining the infected yolk sacs, the TWAR organisms could be seen much more readily. Several passages previously considered negative by Macchiavello staining were found to contain the TWAR organism. Positive cultures usually demonstrated increased numbers of elementary bodies on subsequent passage.

C. Adaptation of TWAR Strains to Grow in Cell Cultures

All but one of the 13 TWAR isolates so far obtained required original inoculation in the yolk sac of embryonated eggs, with egg adaptation of the organisms (one or two passages) prior to cell culture inoculation to successfully adapt most of the TWAR isolates to HeLa 229 cell culture vials.

Serial passages of TWAR organisms were carried out in vial cultures of HeLa 229 cells, modified from the method of Kuo et al. (in "Nongonococcal Urethritis and Related Infections," pp. 328–336, 1977). As described for cell culture isolation (Example 1.A.), three separate HeLa cell monolayers in vials were inoculated for each passage. One was fixed and stained to determine the progress of the infection, and the remaining two monolayers were scraped from the vials and reinoculated exactly as described above for the first passage. At least 10 serial cell culture passages were required for adaptation.

When the infectivity increased so that greater than 50% of the cells were infected, the number of vials inoculated was increased to provide 20 to 30 vials of the infected cells for inoculation into a large culture bottle (32-oz prescription bottle). Serial passages were continued in the bottle culture until 100% of the cells were infected.

EXAMPLE 2

Preparation of TWAR Antigen

Following adaptation of a TWAR strain to 32-oz prescription bottles, the strain was expanded by growth in additional bottles of HeLa 229 cells. The organisms were harvested by rolling the monolayer with glass beads in 20 ml of Hanks balance salt solution. The cells were disrupted by sonication, and the HeLa cell debris was removed by low-speed centrifugation (1,200 rpm for 10 minutes). The organisms were then pelleted by high-speed centrifugation (16,000 rpm for 20 minutes). The TWAR elementary bodies were purified first by cushioning through a 30% Renografin suspension at 16,000 rpm for 40 minutes, which removes approximately 60% of the contaminants, and then by passing through a 30 to 65% Renografin linear gradient at 23,00 rpm for 90 minutes. The suspended band of TWAR elementary bodies were more than 99% purified. The method employed was modified from that of R. S. Stephens et al. (*J. Immunol.* 128: 1083, 1982).

EXAMPLE 3

Immunization Schedule

BALB/c mice were immunized with $5 \times 10^7$ formalin-killed TWAR organisms, intraperitoneally on day 1 and with a similar inoculum intravenously at weekly intervals thereafter for 3 or 4 additional injections. The spleens were harvested 3 days after the last immunization.

EXAMPLE 4

Construction of Hybridomas

The NS-0 myeloma cell line was obtained from Milstein to be used for the fusion procedure. NS-0 cells were routinely grown in RPMI 1640 (GIBCO, Grand Island, N.Y.) containing 15% heat-inactivated fetal calf serum, 1 mM glutamine, and 1 mM pyruvate (referred to as "complete RPMI".)

Spleen cell suspensions were prepared by mincing and passing the cells through a fine nylon screen. Lymphocyte cell suspensions were washed three times in serum-free RPMI; the NS-0 cells were washed once in serum-free RPMI.

NS-0 cells and lymphocytes were fused (at a 1:4 ratio or 1:8 ratio) in 40% polyethylene glycol by centrifugation at $250 \times G$ for 10 minutes. The cells were washed with 10 vol of complete RMPI and centrifuged at $160 \times G$ for 5 minutes. The supernatant was aspirated, and the cells were gently resuspended to $2.5 \times 10^6$ cells/ml in complete RMPI supplemented with HAT medium (complete RMPI containing $1.0 \times 10^{-4}$ M hypoxanthine, $4.0 \times 10^{-7}$ M aminopterin, and $1.6 \times 10^{-5}$ M thymidine). This hybrid cell suspension was mixed with thymocytes from 3- to 5-week-old BALB/c mice to a final concentration of $2.5 \times 10^6$ thymocyltes/ml. The final cell suspension was seeded (in 200 ul volumes) into the wells of 96-well microtest plates (Costar, Cambridge, Mass.). Additional feedings with HAT medium (50% substitution by volume) were given on days 5 and 8. The continued handling, feeding schedule, and cloning by limiting dilution were performed as described by Stephens et al. (supra).

EXAMPLE 5

Screening of Hybridoma Clones

Anti-chlamydial antibodies in culture fluids were detected by enzyme-linked immunosorbent assay (ELISA). For the antibody assay, $1 \times 10^5$ chlamydia organisms in 50 ul of phosphate-buffered saline (PBS, pH 7.6) were adsorbed by the individual wells of a microtest plate by incubation overnight at 37° C. Control plates were prepared by allowing uninfected HeLa 229 cells ($10^4$ cells/well) to attach to wells of microtiter plates. The following morning, the wells of the plates were blocked from further nonspecific protein adsorption by a 2-hour incubation with 75 ul of 5% bovine serum albumin (BSA) in PBS. The antibody assay was performed in three steps:

(1) Fifty microliters of culture fluid were incubated in each of the antigen-adsorbed wells for 60 minutes at 37° C. Nonbound immunoglobulins were then removed from the wells by washing three times with PBS containing 1% BSA.

(2) Peroxidase-conjugated anti-mouse immunoglobulins (50 ul) were added to each well and incubated for 60 minutes at 37° C. Residual unbound peroxidase conjugate was removed by washing three times with PBS.

(3) The immune reactions were detected by adding the substrate o-phenylenediamine and $H_2O_2$, and the color reaction quantitated.

Antibody specificity was further determined by testing the culture supernatants that were positive by ELISA in the micro-IF technique (see Example 6).

EXAMPLE 6

Production of Monoclonal Antibodies

Intraperitoneal inoculation of 1 to $5 \times 10^6$ hybrid cells into syngeneic BALB/c mice induced palpable tumors (hybridomas) within 2 to 3 weeks. To assure tumor induction, syngeneic hosts were primed 2 weeks earlier by an intraperitoneal inoculation of 0.5 ml of Pristane (2, 6, 10, 14-tetramethyl pentadecane, Aldrich Chemical Co., Milwaukee, Wis.). In most instances (>90%), the progressive growth of the intraperitoneal transplanted hybridomas was accompanied by production of ascites fluid (1.0 to 5.0 ml/mouse).

Isotypes of the monoclonal antibodies contained in the ascites fluid were determined by ELISA using the MonoAb-Screen system (Zymed Laboratories, San Francisco, Calif.). Before use, ascites fluids were tested for specific antibody activity by the micro-IF technique.

For the micro-IF assay, culture fluids or ascites fluids were reacted with chlamydia elementary body antigens which were placed on microscope slides for 30 minutes at 37° C. in a moist chamber. After reaction, the slides were washed five times with PBS and air dried. Fluorescein-conjugated anti-mouse immunoglobulins were added and incubated for 30 minutes at 37° C. in a moist chamber. After incubation, the slides were washed five times with distilled water and air dried. A drop of FA mounting fluid was added, and a coverslip was placed on the slide. The reaction was observed under FA-scope. For staining of inclusions, infected HeLa cells were fixed for 10 minutes in absolute methanol and assayed for TWAR-specific antibody activity.

Monoclonal antibodies contained within ascites fluid were affinity purified on a protein A-sepharose column (Pharmacia Fine Chemicals, Uppsala, Sweden). Fluorescein isothiocyanate-conjugated monoclonal antibodies were prepared by the method of Goding (*J. Immunol. Meth.* 13: 215, 1976) and were used at an appropriate dilution as determined by titration for direct immunofluorescence assays. Unconjugated monoclonal antibodies were usually used at 1:100 dilution for indirect immunofluorescence techniques.

EXAMPLE 7

Diagnostic Assay

A. Smear Technique

Monoclonal antibodies to *C. trachomatis* have previously been used for direct fluorescent antibody (FA) assay of smears from clinical specimens. Fluorescein-conjugated monoclonal antibodies specific for TWAR strains of *C. psittaci* have been employed in a similar direct FA assay of respiratory specimens. Briefly, a pharyngeal swab was rolled on a glass slide over two premarked circular areas (5 mm diameter), and the slide was then immersed in 95% ethanol for 10 to 30 minutes. After the slide dried in air, the fluorescent monoclonal antibody conjugate was applied to the specimen area. The slide was incubated at 37° C. for 30 minutes in a moist chamber, washed by briefly dipping through six jars of distilled water, and dried. A drop of Bacto fluorescent antibody mounting fluid (Difco Laboratories, Detroit, Mich.) and a coverslip were applied to the slide, which was then examined under oil immersion at ×500 magnification with an epifluorescence microscope (Carl Zeiss, Oberkochen, West Germany). The entire area of the smear was examined. Findings on slides were considered positive for *C. psittaci* TWAR strain if at least five fluorescing elementary bodies were found in the specimen. Slides with negative findings were read for 5 minutes.

Throat swab smears from six of seven patients with TWAR isolations were stained with fluorescent TWAR monoclonal antibody. In four, typical elementary bodies of chlamydia were demonstrated.

B. Culture Technique

Fluorescein-conjugated TWAR strain-specific monoclonal antibody was used to identify TWAR isolates in initial HeLa 229 cell culture passage. The cell culture isolation technique is described in Example 1.A. Direct fluorescent antibody (FA) staining with TWAR strain-specific monoclonal antibody has greatly facilitated identification of TWAR isolates and has allowed direct passage of these isolates. Each of the TWAR isolates has been identified in primary HeLa 229 cell culture passage by direct FA staining of inclusions.

C. Serological Technique

TWAR antigens, which were mixed with 3% normal yolk sac homogenate (to assist localization and attachment of the antigens on a slide), were dotted on a microscopic slide, air dried, fixed with acetone for 15 minutes, and air dried. Serial twofold dilutions of serum or bodily fluids (such as tears) were applied onto the antigens and incubated for 30 minutes at 30° C. in a moist chamber. Within this assay, the fluids were reacted with chlamydia elementary body antigens. After reaction, the slides were washed five times with PBS and air dried. Fluorescein-conjugated anti-mouse immunoglobulins were added and incubated for 30 minutes at 37° C. in a moist chamber. After incubation, the slides were washed five times with distilled water and air dried. A drop of FA mounting fluid was added, and a coverslip was placed on the slide. The reaction was observed under FA-scope. For staining of inclusions, infected HeLa cells were fixed for 10 minutes in absolute methanol and assayed for TWAR-specific antibody activity.

Table 2 illustrates the high frequency of TWAR antibody present in the sera of adults from seven different areas of the world. Antibody was further found to be present more frequently in males than in females.

TABLE 2

| | Denmark | Helsinki | Nova Scotia | |
|---|---|---|---|---|
| # Tested | 555 | 271 | 200 | |
| | Percent TWAR Antibody | | | |
| Male | 48 | 47 | 35 | |
| Female | 41 | 36 | 18 | |
| | Taiwan | Japan | Panama | Seattle |
| # Tested | 64 | 196 | 934 | 1042 |
| | Percent TWAR Antibody | | | |
| Male | 59 | 45 | — | 45 |
| Female | 52 | — | 40 | 36 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A monoclonal antibody specific for elementary bodies of the TWAR strain of chlamydia, *Chlamydia pneumoniae.*

2. The monoclonal antibody of claim 1 wherein said monoclonal antibody blocks the binding of an antibody produced by cell line RR 402, ATCC Acc. No. H.B. 9109 to said elementary bodies.

3. A continuous hybrid cell line that produces monoclonal antibody specific for elementary bodies of the TWAR strain of clamydia, *Chlamydia pneumoniae.*

4. The cell line of claim 3 wherein the cell line is a hybrid of an immune spleen cell capable of producing antibodies specific to the TWAR strain, and a myeloma cell.

5. The cell line RR 402.

6. A monoclonal antibody produced by the cell line of claim 5, ATCC Acc. No. HB 9109.

7. A method for detecting the presence of the TWAR strain of chlamydia, *Chlamydia pneumoniae*, in a biological sample, comprising:

exposing a biological sample suspected of containing the TWAR strain to a monoclonal antibody specific for elementary bodies of the TWAR strain; and detecting the presence of immunocomplexes formed between the monoclonal antibody and the TWAR strain.

8. The method of claim 7 wherein the monoclonal antibody is labeled.

9. The method of claim 7 wherein the step of detecting comprises contacting the reaction mixture with a labeled specific binding partner for the antibody and detecting the label.

10. The method of claim 8 or 9 wherein said label is selected from the group consisting of enzymes, fluorophores, radioisotopes, and luminescers.

11. The method of claim 7 wherein the step of detecting is by enzyme reaction, fluorescence, luminescence emission, or radioactivity.

12. The method of claim 7 wherein the biological sample is selected from the group consisting of bodily secretions, bodily fluids, and tissue specimens.

13. The method of claim 7 wherein said monoclonal antibody is produced by the cell lines RR 402, ATCC Acc. No. HB 9109.

14. A method for determining the presence of antibodies to the TWAR strain of chlamydia, *Chlamydia pneumoniae*, in a biological sample, comprising:
   incubating the biological sample with elementary bodies of the TWAR strain of chlamydia to form a reaction mixture; and
   detecting the formation of immunocomplexes and therefrom determining the presence of antibodies to the TWAR strain.

15. The method of claim 14 wherein the step of detecting comprises contacting the reaction mixture with a labeled specific binding partner for the antibody and detecting the label.

16. The method of claim 15 wherein the specific binding partner is selected from the group consisting of goat anti-human IgM and goat anti-human IgG.

17. The method of claim 15 wherein said label is selected from the group consisting of enzymes, fluorophores, radioistopes, and luminescers.

18. The method of claim 14 wherein the biological sample is selected from the group consisting of bodily secretions, bodily fluids, and tissue specimens.

19. A method for detecting the presence of the TWAR strain of chlamydia, *Chlamydia pneumoniae* in a biological sample, comprising:

combining a biological sample suspected of containing the TWAR strain with HeLa cells such that the TWAR strain becomes intracellular;
incubating the HeLa cells containing the TWAR strain;
exposing the HeLa cells/TWAR strain to a monoclonal antibody specific for elementary bodies of the TWAR strain; and
detecting the presence of immunocomplexes formed between the TWAR strain and the monoclonal antibody.

20. The method of claim 19 wherein the monoclonal antibody is labeled.

21. The method of claim 19 wherein the step of detecting comprises contacting the reaction mixture with a labeled specific binding partner for the antibody and detecting the label.

22. The method of claim 20 or 21 wherein the label is selected from the group consisting of enzymes, fluorophores, radioisotopes, and luminescers.

23. The method of claim 19 wherein the step of detecting is by enzyme reaction, fluorescence, luminescence emission, or radioactivity.

24. The method of claim 19 wherein the step of combining comprises inoculating the HeLa cells with the sample and subsequently centrifuging the inoculated sample onto the HeLa cells.

25. The method of claim 19 wherein the HeLa cells have been pretreated with DEAE-dextran and cyclohexamide.

26. The method of claim 19 wherein the HeLa cells containing the TWAR strain are incubated at 35° C. for approximately 72 hours.

27. The method of claim 19 wherein the step of exposing includes fixing the monolayers with methanol.

28. The method of claim 19 wherein the biological sample is selected from the group consisting of bodily secretions, bodily fluids, and tissue specimens.

29. The method of claim 19 wherein the monoclonal antibody is produced by the cell line RR 402, ATCC Acc. No. HB 9109.

* * * * *

UNITED STATES PATENT AND TRADEMARK OFFICE
CERTIFICATE OF CORRECTION

PATENT NO. : 5,008,186
DATED : April 16, 1991
INVENTOR(S) : J. Thomas Grayston; Cho-chou Kuo; San-pin Wang It is certified that error appears in the above-identified patent and that said Letters Patent is hereby corrected as shown below:

In column 10, claim 3, line 46, please delete "clamydia" and substitute therefor -- chlamydia --.

In column 10, claim 5, line 51, after "402", please delete "." and substitute therefor -- , ATCC Acc. No. HB 9109. --.

In column 10, claim 6, line 53, after "5", please delete ", ATCC Acc. No. HB 9109".

Signed and Sealed this

Twenty-second Day of September, 1992

Attest:

DOUGLAS B. COMER

Attesting Officer     Acting Commissioner of Patents and Trademarks